United States Patent [19]

Shapiro et al.

[11] Patent Number: 5,496,830
[45] Date of Patent: Mar. 5, 1996

[54] INHIBITION OF HEMOFLAGELLATES BY CAMPTOTHECIN COMPOUNDS

[75] Inventors: Theresa A. Shapiro, Towson; Annette L. Bodley, Elkton, both of Md.; Monroe E. Wall, Chapel Hill; Mansukh C. Wani, Durham, both of N.C.

[73] Assignees: Johns Hopkins University, Baltimore, Md.; Research Triangle Institute, Research Triangle Park, N.C.

[21] Appl. No.: 305,603

[22] Filed: Sep. 14, 1994

[51] Int. Cl.$^6$ .......................... A61K 31/395; A61K 31/55; A61K 31/54; A61K 31/535

[52] U.S. Cl. .......................... 514/283; 514/210; 514/211; 514/212; 514/218; 514/222.2; 514/222.5; 514/223.8; 514/226.8; 514/227.8; 514/228.8; 514/229.2; 514/235.5; 514/254; 514/255; 514/256; 514/279

[58] Field of Search .................. 514/210, 211, 514/212, 218, 222.2, 222.5, 223.8, 226.8, 227.8, 228.8, 229.2, 235.5, 254, 255, 256, 279, 283

[56] References Cited

U.S. PATENT DOCUMENTS 5,364,858  11/1994  Wall et al. .............................. 514/279

OTHER PUBLICATIONS

CA 108:215899, Chakraborty et al., 1988.

*Primary Examiner*—Kimberly Jordan
*Attorney, Agent, or Firm*—Oblon, Spivak, McClelland, Maier & Neustadt

[57] ABSTRACT

Camptothecin compounds are effective inhibitors of hemoflagellate growth and are useful in treating leishmaniasis and trypanosomiasis in livestock, other domestic animals and humans.

19 Claims, No Drawings

INHIBITION OF HEMOFLAGELLATES BY CAMPTOTHECIN COMPOUNDS

BACKGROUND OF THE INVENTION

1. Field of the Invention

This invention relates to the inhibition of flagellated parasitic protozoa Trypanosoma and Leishmania with camptothecin compounds. Camptothecin compounds have the ring structure shown below.

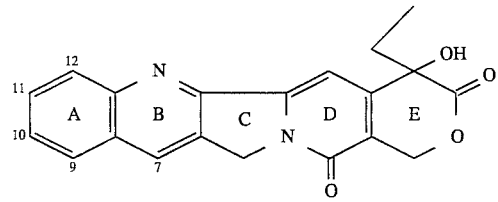

The invention also relates to the treatment of animals having hemoflagellate infections with camptothecin compounds.

2. Background of the Invention

The hemoflagellates include organisms of the genera Trypanosoma and Leishmania.

Organisms of the genus Trypanosoma are hemoflagellates which infect livestock, wild animals and humans causing trypanosomiasis. Diseases associated with trypanosomiasis include sleeping sickness, Chagas' Disease and asymptomatic trypanosomiasis. Trypanosomiasis is particularly prevalent in African and South American countries.

Current therapy for trypanosomiasis has many drawbacks. The existing pharmaceuticals for treating trypanosomiasis in humans include suramin, pentamidine, stilbamidine, propamidine, melarsoprol, nitrofurazone and the trivalent arsenicals. These drugs are toxic and generally must be administered parenterally. Trypanosome strains resistant to these drugs are now emerging. A more recent pharmaceutical introduced into clinical use is α-difluoromethylornithine. See Bacch, C. J. et a.l. (1980) *Science*, 210:332–334. This compound is available on a limited basis only, however, and requires repeated high parenteral doses to effect a cure. Additionally, this compound is ineffective against Rhodesian sleeping sickness.

Conventional therapy for livestock and other domestic animals includes treatment with diminazene aceturate (berenil), isometamidium chloride (samorin) and ethidium bromide. See Williamson, J. (1970) in *The African Trypanosomiases* (Mulligan, H. W., Ed.) pages 125–221, Wiley-Interscience, Great Britain.

Organisms of the genus Leishmania are hemoflagellates which are closely related to trypanosomes and are the causative agent of the disease leishmaniasis. This disease is spread by the bite of sand flies, and on a worldwide basis, afflicts millions of persons. In recent years, American soldiers serving in Panama, the middle east and East Africa have returned home with leishmaniasis. Untreated, some forms of leishmaniasis, notably visceral leishmaniasis are fatal.

Current therapy for leishmaniasis includes pentavalent antimonials, pentamidine, and amphotericin B, all of which have substantial toxicity. See Neva, F. and Sacks, D. (1990) in Tropical and Geographical Medicine, 2nd Ed. (Warren, K. S. and Mahmoud, A. A. F., Eds.) pages 296–308, McGraw-Hill, N.Y.

A need continues to exist for new compounds which are toxic to hemoflagellates and useful in treating trypanosomiasis and leishmaniasis.

SUMMARY OF THE INVENTION

Accordingly, one object of the present invention is to provide compounds which are cytotoxic to and can be used to inhibit organisms of the genera Trypanosoma and Leishmania.

A further object is to provide compounds which are useful in treating trypanosomiasis and leishmaniasis in livestock, domestic animals and humans.

These and other objects which will become apparent from the following specification have been achieved by the discovery that camptothecin and derivatives thereof are cytotoxic to hemoflagellates and are useful in treating trypanosomiasis and leishmaniasis in animals and humans.

DETAILED DESCRIPTION OF THE PREFERRED EMBODIMENTS

Infective trypanosomes are introduced through the bite of the tsetse fly and multiply at the site of inoculation to cause swelling which then progresses to a trypanosoma chancre, spreading to lymph nodes, blood stream and in terminal stages to the central nervous system where it produces the typical symptoms of sleeping sickness including lethargy, lack of appetite, unconsciousness and possible death. In addition to sleeping sickness, trypanosome infection causes asymptomatic trypanosomiasis and Chagas' Disease. Chagas' Disease is contracted from reduviid bugs or from contaminated blood transfusions. Early symptoms include a local reaction at the site of inoculation, and generalized lymphadenopathy and hepatosplenomegaly. Chronic disease includes cardiomyopathy and arrhythmias, megaesophagus and megacolon. In the present invention, camptothecin and derivatives thereof have been found to effectively inhibit the trypanosomes responsible for these diseases.

Specific trypanosomes which are inhibited by camptothecin compounds include *T. brucei brucei*, including *T. brucei rhodensiense* and *T. brucei gambiense* which are considered to be subspecies of *T. brucei*. Additional trypanosomes which may be treated with camptothecin compounds include *T. equiperdum*, *T. cruzi* the causative agent of Chagas' disease and *T. rangeli* which infects many children in South American countries.

Infective Leishmania are introduced through the bite of an infected female phlebotomine sand fly. The infective form of Leishmania is called a metacyclic promastigote which is deposited in the skin when the sand fly bites. The organs primarily affected are the liver, spleen, bone marrow and the reticuloendothelial system. The spleen and liver become enlarged contributing to anemia and thrombocytopenia which are characteristic of visceral leishmaniasis. In the present invention, camptothecin and derivatives thereof have been found to effectively inhibit Leishmania hemoflagellates which are responsible for both cutaneous and visceral leishmaniasis.

The specific Leishmania hemoflagellates which are inhibited by camptothecin compounds include *L. mexicana*, including *L.m. mexicana*, *L.m. amazonensis* and *L.m. venezuelensis*, *L. braziliensis* including *L.b. braziliensis*, *L.b. guyanensis*, *L.b. panamensis* and *L.b. peruviana*, *L. major*, *L. tropica*, *L. aethiopica*, *L. donovani*, *L. infantum* and *L. chagasi*.

An important aspect of this invention is the discovery that the antihemoflagellate activity of camptothecin compounds correlates closely with the activity of these compounds as inhibitors of the enzyme topoisomerase I. It has been discovered that camptothecin compounds which actively inhibit the enzyme topoisomerase I in conventional in vitro tests are effective inhibitors of hemoflagellates.

Any pharmaceutically or veterinarially acceptable camptothecin compound or salt thereof exhibiting topoisomerase I inhibiting activity may be used in the present invention. By "exhibiting topoisomerase I inhibiting activity" is meant a camptothecin compound which exhibits an $IC_{50}$ value for topoisomerase I inhibition by the clearable complex assay of Hsiang et al. of 1.0 μM or less. The ability of camptothecin compounds to inhibit the enzyme topoisomerase I can be readily evaluated using the cleavable complex assay described in U.S. Pat. No. 5,244,903 and Hsiang et al., (1985), *J. Biol Chem.*, 260:14875–14878. Particularly preferred compounds are camptothecin derivatives having the (S) configuration at the 20-position and exhibiting topoisomerase I inhibitory activity equal to or greater than the activity of 20(S)-camptothecin (referred to below as 20(S)-CPT).

Camptothecin compounds and salts thereof which are known to exhibit topoisomerase I inhibitory activity are described, for example, in U.S. Pat. Nos. 4,894,456, 4,981, 968, 5,053,512, 5,049,668, 5,106,742, 5,180,722, 5,244,903, 5,227,380, 5,122,606, 5,122,526, 5,225,404, 4,914,205, 4,545,880, 4,604,463, 4,473,692, 4,031,098, EP 0 220 601, EP 0 074 256 and U.S. Patent application Ser. Nos. 07/784, 275 and 07/826,729 (EP 0 540 099). These U.S. applications and U.S. Patents are incorporated herein by reference for a more complete description of camptothecin compounds which can be used in the present invention.

Camptothecin and derivatives thereof have an asymmetric carbon atom at the 20-position and, therefore, exist in two enantiomeric forms, i.e. the (R) and (S) configurations. This invention includes both enantiomeric forms and all combinations of these forms, including racemic mixtures designated as (RS).

Preferred camptothecin compounds for use in the method of the present invention are 20(S)-CPT and derivatives thereof in which the A ring is unsubstituted or there is a substituent at the 9-, 10- or 9- and 10,11-positions. Suitable compounds have the structure shown below.

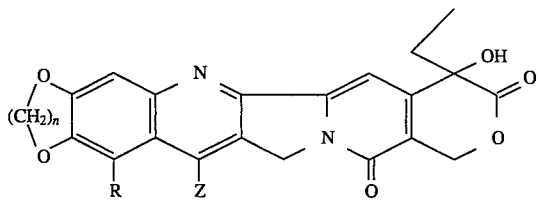

In the structure shown above, R is $NO_2$, $NH_2$, $N_3$, hydrogen, halogen (F, Cl, Br, I), COOH, OH, O-$C_{1-3}$ alkyl, SH, S-$C_{1-3}$ alkyl, CN, $CH_2NH_2$, NH-$C_{1-3}$ alkyl, $CH_2$-NH-$C_{1-3}$ alkyl, N($C_{1-3}$ alkyl)$_2$, $CH_2N(C_{1-3}$ alkyl)$_2$, O-, NH- and S-$CH_2CH_2N(CH_2CH_2OH)_2$, O-, NH- and S-$CH_2CH_2CH_2N(CH_2CH_2OH)_2$, O-, NH- and S-$CH_2CH_2N(CH_2CH_2CH_2OH)_2$, O-, NH- and S-$CH_2CH_2CH_2N(CH_2CH_2CH_2OH)_2$, O- NH- and S-$CH_2CH_2N(C_{1-3}$ alkyl)$_2$, O-, NH- and S-$CH_2CH_2CH_2N(C_{1-3}$ alkyl)$_2$, CHO or $C_{1-3}$ alkyl. Preferred compounds are those in which R is halogen, nitro or amino.

Z in the structure shown above is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (6) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl or $C_{1-6}$ alkoxy-$C_{1-6}$ alkyl and $R^2$ is -$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and -$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups. In the structure shown above, n is an integer of 1 or 2.

Preferred aryl groups are phenyl and naphthyl. Also preferred are compounds having the structure shown above where Z is methyl, ethyl or propyl.

Preferred camptothecin compounds which are preferably substituted in the 9- or 10- position and can be used in the present invention have the structure shown below.

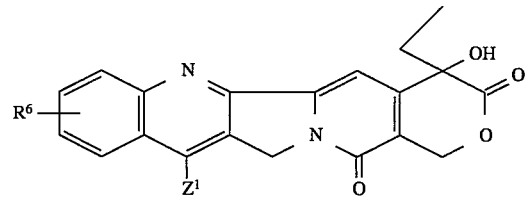

In this structure, $R^6$ is hydrogen, cyano, formyl, hydroxy, $C_{1-8}$ alkoxy, nitro, amino, halogen (I, Br, Cl, F), $C_{1-8}$ alkyl, trifluoromethyl, aminomethyl, azido, amido, hydrazino, $OC(O)R^7$ or $OC(O)-NR^7R^8$, where $R^7$ and $R^8$ are, independently, hydrogen or $C_{1-8}$ alkyl and $Z^1$ has the same definition as Z described above, preferably methyl, ethyl or propyl.

The lactone ring of the camptothecin compounds shown above may be opened by alkali metal or alkaline earth metal bases, for example, sodium hydroxide or calcium hydroxide to form alkali metal or alkaline earth metal salts of the open ring form of the camptothecin compounds. Open ring compounds have better solubility in water.

The preparation of these preferred compounds is described in U.S. Pat. Nos. 4,894,456, 5,180,722 and EP 0 540,099.

Additional camptothecin compounds which may be used in the present invention are camptothecin compounds in which the hydroxyl group at the 20-position has been esterified with the alpha-carboxyl group of a naturally occurring amino acid to form a group of the formula -$OC(O)-(CH_2)_m-NR^{10}R^{11}$, where m=1–6 or -$OC(O)CHR^9NR^{10}R^{11}$, where $R^9$ is the side chain of one of the naturally occurring α-amino acids, $R^{10}$ and $R^{11}$ are, independently, hydrogen or $C_{1-8}$ alkyl. Suitable side chains $R^9$ are the side chains of the amino acids glycine, alanine, valine, leucine, isoleucine, phenylalanine, tyrosine, tryptophan, lysine, arginine, histidine, aspartate, glutamate, asparagine, glutamine, cysteine and methionine. Particularly preferred esters are glycinate esters. These esters are prodrugs which are converted to the camptothecin compound by hydrolysis of the ester bond. The esters may be prepared by the method described in U.S. Pat. No. 4,943,579 which is incorporated herein by reference for a more complete description of the process of preparing the esters and for a description of suitable esters formed by the process.

Particularly preferred compounds are selected from the group consisting of 7-methyl-10,11-methylenedioxy-20(S)-camptothecin, 7-ethyl-10,11-methylenedioxy-20(S)-camptothecin, 7-ethyl-9-amino-10,11-methylenedioxy-20(S)-camptothecin, 7-ethyl- 9-nitro-10,11-methylenedioxy-20(S)-camptothecin, 7-ethyl- 10-nitro-20(S)-camptothecin, 7-ethyl-10-amino-20(S)-camptothecin, 7-ethyl-20(S)-camptothecin, 7-propyl-20(S)-camptothecin, 7-ethyl-9-amino-20(S)-camptothecin, 7-ethyl-9-nitro- 20(S)-camptothecin, 9-amino-10,11-methylenedioxy-20(S)-camptothecin, 9-chloro-10,11-methylenedioxy-20(S)-camptothecin, 10,11-methylenedioxy-20(S)-camptothecin, 9-chloro- 20(S)-camptothecin, 10,11-methylenedioxy-20-glycinate- 20(S)-camptothecin, 9-amino-20(S)-camptothecin, 10-amino-20(S)-camptothecin, 10-chloro-20(S)-camptothecin and 20(S)-camptothecin.

The method of the present invention, i.e., inhibiting the growth of hemoflagellates by contacting the organisms with a camptothecin compound which inhibits the enzyme topoisomerase I, is useful as a control in screening assays in which hemoflagellate strains are assayed for their sensitivity to known anti-hemoflagellate chemotherapeutic drugs. In these assays, the drug-resistance of a particular hemoflagellate strain can be determined by growing the strain in the presence of specific anti-hemoflagellate compounds as positive controls. For example, when a strain is discovered which is resistant to known drugs, the strain should be assayed for its resistance to a battery (plurality) of known anti-hemoflagellate drugs including a plurality of the camptothecin compounds of the present invention. The assay provides a means of determining which single camptothecin compound or which combination of camptothecin compounds or combination of a camptothecin compound and conventional anti-hemoflagellate compound are best suited to inhibit growth of the strain. Typically, the assay will use the positive control compounds at a variety of concentrations to determine the $EC_{50}$ value for the specific compound against the strain. The assay procedure and the specific concentrations of positive control compounds can be readily determined by one having ordinary skill in this art using the assay described in the example. Table 1 below provides an example of an assay.

The camptothecin compounds are administered in a dose which is effective to inhibit the pathogenic form of the hemoflagellates. As used herein, an effective amount of the hemoflagellate inhibiting camptothecin compounds is intended to mean an amount of the compound that will inhibit the growth of growing hemoflagellates, that is, reduce the number of growing hemoflagellates relative to a control in which the hemoflagellates are not treated with the camptothecin compound. These effective amounts are generally from about 1– 60 mg/kg of body weight per week, preferably about 2–20 mg/kg per week.

The compounds of the present invention may be administered as a pharmaceutical or veterinary composition containing the camptothecin compound and a pharmaceutically or veterinarially acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

The compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. Nos. 4,452,747, 4,448, 765, 4,837,028, 4,721,612, 4,594,241, 4,302,459 and 4,186, 183. The disclosures of these U.S. Patents are incorporated herein by reference. Suitable liposome preparations for use in the present invention are also described in WO-9318749-A1, J-02056431-A and EP-276783-A. The compounds of the present invention may be formulated according to these methods and administered in liposome microvesicles.

The camptothecin compounds may be used individually to inhibit the growth of hemoflagellates. Alternatively, combinations of two or more camptothecin compounds may be used or combinations of one or more camptothecin compounds with one or more known anti-hemoflagellate compounds such as suramin, pentamidene, stilbamine, propamidine, melarsoprol, nitrofurazone, trivalent arsenicals, diminazene aceturate, isometamidium chloride, ethidium bromide, pentavalent antimonials, amphotericin B, etc. When a camptothecin compound is combined with a conventional anti-hemoflagellate compound, the camptothecin compound will generally be present in an amount ranging from about 1–99 wt. %, preferably, 5–95 wt. % of the combined amount of camptothecin and conventional anti-hemoflagellate compound. The pharmaceutical and veterinary compositions noted above may contain these combinations of compounds together with an acceptable carrier or diluent.

In addition to treatment of humans, the camptothecin compounds of the present invention may be used to inhibit growth of hemoflagellates in livestock animals such as cows, horses, pigs, sheep and goats as well as in domesticated animals such cats and dogs.

A further important aspect of the present invention is the overall low toxicity of the camptothecin compounds when administered as described herein. The low toxicity of camptothecin compounds when administered for antitumor therapy is described, for example, in U.S. Pat. No. 5,225,404.

The compounds of the present invention are also useful for decontaminating blood samples obtained from a mammal to eliminate the presence of hemoflagellates in the sample. In this utility, a blood sample is treated by the addition of one or more of the camptothecin compounds of the present invention in an amount sufficient to kill all hemoflagellates present in the sample. The amount of camptothecin mixed with the blood sample is obviously dependent upon the volume of the sample, and can be readily determined by one having ordinary skill in the art based on the $EC_{50}$ values presented in Table 1 below. Generally, an excess of camptothecin compound is added to the blood sample to ensure complete removal of hemoflagellates.

Other features of the invention will become apparent in the course of the following descriptions of exemplary embodiments which are given for illustration of the invention and are not intended to be limiting thereof.

EXAMPLES

Camptothecin compounds were tested against blood stream form trypanosomes in vitro. *T. brucei brucei* (MiTat 1.2, strain 427, variant 221) were cultured at 37° C. according to the methods of Carruthers and Cross (Carruthers, V. B., and Cross, G. A. M. (1992) *Proc. Natl. Acad. Sci. USA.*, 89:8818– 8821) with the substitution of phenol red-free Iscoves Modified Dulbecco's Medium (Mediatech, Inc.) in the HMI-9 culture medium. Stock solutions of camptothecin compounds were prepared in 100% dimethylsulfoxide (Aldrich). Exponentially growing trypanosomes were diluted to $10^5$ cells/ml with prewarmed medium.

Diluted trypanosomes (199 µl per well) were added to a 96 well microtitre plate (Costar No. 3595) containing the camptothecin solutions or dimethylsulfoxide alone (1 µl per well). Each camptothecin concentration was tested in quadruplicate. The plate was incubated at 37° C. for 24 h in a humidified incubator maintained with 5% $CO_2$.

Surviving trypanosomes were detected by the acid phosphatase method (Martin, A. and Clynes, M. (1991) *In Vitro Cell. Dev. Biol.* 27A:183–184). p-Nitrophenol phosphate (20 µl of 20 mg/ml; solubilized in 1 M sodium acetate, pH 5.5; 1% Triton X-100) was added to each 200 µl sample and mixed. The plate was then incubated for 3–4 h at 37° C. The production of p-nitrophenol was measured at 405 nm on a microplate reader ($UV_{max}$ kinetic microplate reader, Molecular Devices). Quadruplicate values were averaged and blanks (complete reaction mixture without trypanosomes) were subtracted for each drug concentration. Data were plotted on semilog graphs to obtain the $EC_{50}$ values listed in Table 1.

Table 1 also shows topoisomerase I inhibitation data ($IC_{50}$) for numerous camptothecin compounds. Topoisomerase I inhibition relative to 20(S)-camptothecin was also determined in separate independent experiments. These relative potency values are also shown in Table 1.

Obviously, numerous modifications and variations of the present invention are possible in light of the above teachings. It is, therefore, to be understood that within the scope of the appended claims, the invention may be practiced otherwise than as specifically described herein.

TABLE 1

Effect of Camptothecin and Analogs on Topoisomerase I Inhibition and Inhibition of Trypanosomes (*T. brucei*)

| Compound | T-1 Inhibition[a] (µM) $IC_{50}$ | Relative Potency T-1 Inhibition[b] | Trypanosome (µM) $EC_{50}$ |
|---|---|---|---|
| 7-Methyl-10,11-methylenedioxy-20(S)-CPT | — | 5 | 0.04 |
| 7-Ethyl-10,11-methylenedioxy-20(S)-CPT | — | 12 | 0.06 |
| 7-Ethyl-9-amino-10,11-methylenedioxy-20(S)-CPT | — | 10 | 0.06 |
| 9-Amino-10,11-MD-20(S)-CPT* | 0.05 | — | 0.18 |
| 7-Ethyl-9-nitro-10,11-methylenedioxy-20(S)-CPT | — | 5 | 0.21 |
| 10,11-MD-20(S)-CPT | 0.03 | 10 | 0.21 |
| 9-Nitro-10,11-methylenedioxy-20(S)-CPT | — | 3 | 0.40 |
| 7-Ethyl-10-nitro-20(S)-CPT | — | 4 | 0.60 |
| 7-Ethyl-10-amino-20(S)-CPT | — | 5 | 0.62 |
| 7-Ethyl-20(S)-CPT | — | 3 | 0.77 |
| 7-Propyl-20(S)-CPT | — | 2 | 0.77 |
| 9-Amino-20(S)-CPT | 0.11 | 2 | 0.87 |
| 9-Chloro-20(S)-CPT | 0.09 | — | 0.89 |
| 7-Ethyl-9-amino-20(S)-CPT | — | 5 | 0.91 |
| 10,11-MD-20-Glycinate-20(RS)-CPT | 0.43 | — | 0.92 |
| 10-Amino-20(S)-CPT | 0.14 | 2 | 1.20 |
| 20(S)-CPT | 0.68 | 1 | 1.55 |
| 9-Nitro-20(S)-CPT | — | — | 1.64 |
| 10-Nitro-20(S)-CPT | — | — | 1.75 |
| 10-Chloro-20(S)-CPT | 0.14 | — | 1.77 |
| 7-Ethyl-9-nitro-20(S)-CPT | — | 4 | 2.67 |
| 10-Methyl-20(S)-CPT | — | — | 3.14 |
| 20-Glycinate-20(S)-CPT | — | — | 5.10 |
| 12-Amino-20(S)-CPT | inactive | — | 22.5 |
| 11-Amino-20(S)-CPT | inactive | — | 23.1 |

*MD = methylenedioxy, CPT = camptothecin
[a]T-1 = topoisomerase I inhibition by the cleavable complex assay of Hsiang et al.
[b]T-1 relative to 20(S)-CPT.

What is claimed as new and desired to be secured by Letters Patent of the United States is:

1. A method of inhibiting hemoflagellate growth, comprising contacting living hemoflagellates with an effective inhibitory amount of a camptothecin compound wherein said compound exhibits hemoflagellate topoisomerase I inhibitory activity.

2. The method of claim 1, wherein said camptothecin compound exhibits an $IC_{50}$ value of 1.0 µM or less in a cleavable complex assay for topoisomerase I inhibitory activity.

3. The method of claim 1, wherein said camptothecin compound has the structure shown below

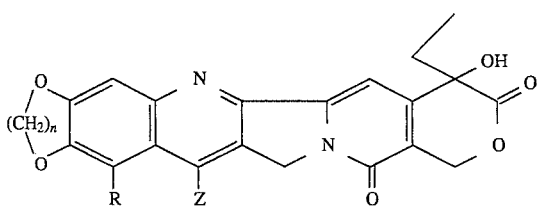

wherein in the structure shown above, R is $NO_2$, $NH_2$, $N_3$, hydrogen, halogen, COOH, OH, $O-C_{1-3}$ alkyl, SH, $S-C_{1-3}$ alkyl, CN, $CH_2NH_2$, $NH-C_{1-3}$ alkyl, $CH_2-NH-C_{1-3}$ alkyl, $N(C_{1-3}$ alkyl$)_2$, $CH_2N(C_{1-3}$ alkyl$)_2$, O-, NH- and $S-CH_2CH_2N(CH_2CH_2OH)_2$, O-, NH- and $S-CH_2CH_2CH_2N(CH_2CH_2OH)_2$, O-, NH- and $S-CH_2CH_2N(CH_2CH_2CH_2OH)_2$, O-, NH- and $S-CH_2CH_2CH_2N(CH_2CH_2CH_2OH_2)_2$, O-, NH- and $S-CH_2CH_2N(C_{1-3}$ alkyl$)_2$, O-, NH- and $S-CH_2CH_2CH_2N(C_{1-03}$ alkyl$)_2$, CHO or $C_{1-3}$ alkyl;

Z in the structure shown above is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (6) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy- $C_{1-6}$ alkyl or $C_{1-6}$ alkoxy-$C_{1-6}$ alkyl and $R^2$ is -$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and -$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

n is an integer of 1 or 2; and pharmaceutically or veterinarially acceptable salts thereof.

4. The method of claim 1, wherein said camptothecin compound has the structure shown below

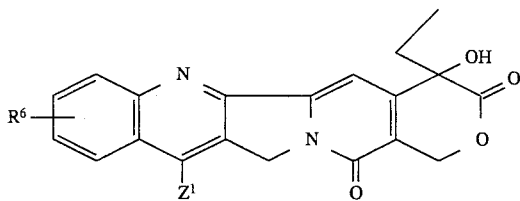

wherein $R^6$ is hydrogen, cyano, formyl, hydroxy, $C_{1-8}$ alkoxy, nitro, amino, halogen, $C_{1-8}$ alkyl, trifluoromethyl, aminomethyl, azido, amido, hydrazino, $OC(O)R^7$ or $OC(O)NR^7R^8$ where $R^7$ and $R^8$ are, independently, hydrogen or $C_{1-8}$ alkyl; and $Z^1$ is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (6) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy- $C_{1-6}$ alkyl or $C_{1-6}$ alkoxy-$C_{1-6}$ alkyl and $R^2$ is -$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{1-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and -$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups.

5. The method of claim 3, wherein the OH group at the 20-position of said camptothecin compound is esterified to form a group of the formula -$OC(O)CHR^9NR^{10}R^{11}$, where $R^9$ is the side chain of a naturally occurring α-amino acid and $R^{10}$ and $R^{11}$ are, independently, hydrogen or $C_{1-8}$ alkyl.

6. The method of claim 4, wherein the OH group at the 20-position of said camptothecin compound is esterified to form a group of the formula -$OC(O)CHR^9NR^{10}R^{11}$, where $R^9$ is the side chain of a naturally occurring α-amino acid and $R^{10}$ and $R^{11}$ are, independently, hydrogen or $C_{1-8}$ alkyl.

7. The method of claim 1, wherein said camptothecin compound is selected from the group consisting of 7-methyl- 10,11-methylenedioxy-20(S)-camptothecin, 7-ethyl-10,11-methylenedioxy-20 (S)-camptothecin, 7-ethyl-9-amino-10,11-methylenedioxy- 20(S)-camptothecin, 7-ethyl-9-nitro-10,11-methylenedioxy- 20(S)-camptothecin, 7-ethyl-10-nitro-20(S)-camptothecin, 7-ethyl-10-amino-20(S)-camptothecin, 7-ethyl- 20(S)-camptothecin, 7-propyl-20(S)-camptothecin, 7-ethyl- 9-amino-20(S)-camptothecin, 7-ethyl-9-nitro-20(S)-camptothecin, 9-amino-10,11-methylenedioxy-20(S)-camptothecin, 9-chloro- 10,11-methylenedioxy-20(S)-camptothecin, 10,11-methylenedioxy- 20(S)-camptothecin, 9-chloro-20(S)-camptothecin, 10,11-methylenedioxy-20-glycinate-20(S)-camptothecin, 9-amino-20(S)-camptothecin, 10-amino-20(S)-camptothecin, 10-chloro-20(S)-camptothecin and 20(S)-camptothecin.

8. The method of claim 7, wherein the OH group at the 20-position of said camptothecin compound is esterified to form a group of the formula -$OC(O)CHR^9NR^{10}R^{11}$, where $R^9$ is the side chain of a naturally occurring α-amino acid and $R^{10}$ and $R^{11}$ are independently, hydrogen or $C_{1-8}$ alkyl.

9. The method of claim 1, wherein the hemoflagellate is selected from the group consisting of Trypanosoma organisms.

10. The method of claim 1, wherein said hemoflagellate is selected from the group consisting of Leishmania organisms.

11. The method of claim 1, wherein said contacting comprises administering said camptothecin compound to a mammal.

12. The method of claim 11, wherein said effective inhibitory amount comprises 1–60 mg/kg of body weight per week.

13. The method of claim 12, wherein said effective inhibitory amount comprises about 2–20 mg/kg of body weight per week.

14. The method of claim 12, comprising parenterally administering said camptothecin compound to said mammal.

15. The method of claim 12, comprising orally administering said camptothecin compound to said mammal.

16. The method of claim 12, wherein said mammal is selected from a group consisting of cows, horses, pigs, sheep, goats, cats, and dogs.

17. The method of claim 12, wherein said mammal is a human.

18. A pharmaceutical or veterinary composition for inhibiting hemoflagellate growth comprising a camptothecin compound which inhibits hemoflagellate topoisomerase I and exhibits an $IC_{50}$ value of 1.0 µM or less in a cleavable complex assay for topoisomerase I inhibitory activity and a compound selected from the group consisting of suramin, pentamidene, stilbamine, propamidine, melarsoprol, nitrofurazone, diminazene aceturate, isometamidium chloride, ethidium bromide, pentavalent antimonials, amphotericin B.

19. The composition of claim 18, comprising 1–99 wt. % of said camptothecin compound.

* * * * *

UNITED STATES PATENT AND TRADEMARK OFFICE
CERTIFICATE OF CORRECTION

PATENT NO. : 5,496,830
DATED : March 5, 1996
INVENTOR(S) : Theresa SHAPIRO et al.

It is certified that error appears in the above-indentified patent and that said Letters Patent is hereby corrected as shown below:

On the title page, Item [73], the second Assignee is spelled incorrectly. It should read:

--[73] Assignees: Johns Hopkins University, Baltimore, Md.; Research Triangle Institute, Research Triangle Park, N.C.--

Signed and Sealed this

Twenty-first Day of May, 1996

Attest:

BRUCE LEHMAN

*Attesting Officer*            *Commissioner of Patents and Trademarks*